United States Patent [19]

Vo-Dinh

[11] Patent Number: 5,599,717
[45] Date of Patent: Feb. 4, 1997

[54] ADVANCED SYNCHRONOUS LUMINESCENCE SYSTEM

[75] Inventor: Tuan Vo-Dinh, Knoxville, Tenn.

[73] Assignee: Martin Marietta Energy Systems, Inc., Oak Ridge, Tenn.

[21] Appl. No.: 300,202

[22] Filed: Sep. 2, 1994

[51] Int. Cl.$^6$ .................................................. G01N 21/64
[52] U.S. Cl. ........................ 436/63; 436/64; 436/171; 436/172
[58] Field of Search ........................ 436/63, 64, 171, 436/172; 422/82.05, 82.08; 128/633, 634

[56] References Cited

U.S. PATENT DOCUMENTS

| | | |
|---|---|---|
| 4,930,516 | 6/1990 | Alfano et al. . |
| 5,042,494 | 8/1991 | Alfano . |
| 5,131,398 | 7/1992 | Alfano et al. . |
| 5,261,410 | 11/1993 | Alfano et al. . |
| 5,272,089 | 12/1993 | Vo-Dinh . |
| 5,303,026 | 4/1994 | Strobl et al. . |
| 5,306,403 | 4/1994 | Vo-Dinh . |
| 5,318,751 | 6/1994 | Vo-Dinh . |

OTHER PUBLICATIONS

*Autofluorescence of Normal and Malignant Bronchial Tissue*, by Jaclyn Hung MSc, Stephen Lam, MD, Jean C. LeRiche, MBChB, and Banko Palcic, PhD (Lasers in Surgery and Medicine 11:99–105 (1991).

*Multicomponent Analysis by Synchronous Luminescence Spectrometry*, by Tuan Vo–Dinh (Reprinted from Analytical Chemistry, vol. 50, p. 396, Mar. 1978).

*Synchronous Excitation Spectroscopy*, by T. Vo–Dinh (From: Modern Fluorescence Spectroscopy vol. 4; Plenum Publishing Corp., 1981).

Rao, C. M. "Synchronous Scan Fluorescence Spectroscopy of Proteins and Human Eye Lenses" Biochemical and Biophysical Research Communications, vol. 176, No. 3 (1991) pp. 1351–1357.

Manchester, D. K. et al. "Detection of benzo(a)pyrene diol epoxide–DNA adducts in human placenta" Proc. Nat. Acad. Sci. USA, vol. 85 (1988) pp. 9243–9247.

Rubio, S. et al. "Analytical Applications of Synchronous Fluorescence Spectroscopy" Talanta, vol. 33, No. 8 (1986) pp. 633–640.

*Primary Examiner*—Jeffrey Snay
*Attorney, Agent, or Firm*—Edward A. Pennington; W. Mark Bielawski; Joseph A. Marasco

[57] ABSTRACT

A method and apparatus for determining the condition of tissue or otherwise making chemical identifications includes exposing the sample to a light source, and using a synchronous luminescence system to produce a spectrum that can be analyzed for tissue condition.

10 Claims, 9 Drawing Sheets

CYCLES:

$t_1 : \lambda_1 \rightarrow$ excitation cycle $t_2 : \lambda_1 + \Delta\lambda \rightarrow$ emission cycle $t_3 : \lambda_2 \rightarrow$ excitation cycle $t_4 : \lambda_2 + \Delta\lambda \rightarrow$ emission cycle

ADVANCED SYNCHRONOUS LUMINESCENCE SYSTEM

This invention was made with Government support under contract DE-AC05-84OR21400 awarded by the U.S. Department of Energy to Martin Marietta Energy Systems, Inc. and the Government has certain rights in this invention.

FIELD OF THE INVENTION

The present invention relates generally to the fields of chemical analysis and biomedical diagnostics, and more specifically, to the use of synchronous luminescence to perform biomedical diagnostics. A multi-dye laser source, or a light source coupled to an acousto-optic tunable filter is used to induce from a sample luminescence having a unique spectral signature.

BACKGROUND OF THE INVENTION

Laser-induced fluorescence (LIF) has been investigated recently as a method to discriminate tumors from normal tissues. LIF techniques have also been used to characterize pre-malignant colorectal lesions and to distinguish adenomatone polyps from normal colon tissue and hyperplastic polyps.

Others have investigated the use of LIF to distinguish adenomatous tissue from normal colon tissue in vivo. In these investigations, a laser such as a pulsed nitrogen laser-pumped dye laser system (370 nm) was used as the excitation source. The sensitivity, specificity and predictive value for diagnostics of their technique towards adenomas were reported to be very good. Because only a small number of hyperplastic polyps were examined, it is unclear whether colonic neoplasia can be reliably identified, since it is not known whether the observed differences in fluorescence arise from compositional changes specific to dysplasia or simply from structural differences between polyps and the colon.

The LIF technique has also been used to distinguish adenomatous from normal colon tissue in vitro. In a study conducted by Kapalia et al. in 1990, endoscopically resected polyps were excited using a continuous wave (cw) helium-cadmium laser (325 nm) and the resulting fluorescence of these endoscopically resected polyps was measured with an optical-multichannel-analyzer system. They found that adenomatous polyps (51 of 51) could be reliably distinguished from normal colonic tissue (69 of 69) in vitro based on LIF scores from a stepwise multivariate linear regression (MVLR) analysis of their data. In addition, 15 of 16 hyperplastic polyps fell within the normal colonic tissue range, resulting in the ability to distinguish colonic neoplasia of resected tissue.

Schomacker et al., in 1992, also used a MVLR analysis method to distinguish neoplastic tissue from non-neoplastic tissue. Their data suggested that the LIF measurements sense changes in polyp morphology rather than changes in fluorplores specific to polyps, and it was this change in morphology that leads indirectly to discrimination of polyps. Schomacker concluded that the feasibility of discriminating groups of normal from dysplastic cells by LIF had not yet been demonstrated.

The above examples underscore the fact that, in spite of some specific successes, one of the major limitations of the LIF technique is its specificity. The laser used as the excitation source used under current conditions can yield high intensity but does not provide a selective tool for excitation.

Tissue fluorescence is a complex process arising from the superposition of the fluorescence of many chemical species in tissue. Although changes in fluorescence profiles have been reported by many researchers involved, these changes are often difficult to provide unique "spectral signatures" useful for unequivocal diagnostic purposes.

In addition to spectral specificity problems, current instrumentation for cancer diagnostics have serious limitations. A laser-based LIF instrument can use only fixed excitation whereas conventional spectrometers (non-laser devices) do not provide rapid synchronous luminescence (SL) scanning capabilities for useful clinical applications.

There is, therefore, a strong need to develop new or improved methods and instrumentation for sensitive as well as selective chemical analysis and biomedical diagnostics.

SUMMARY OF THE INVENTION

An object of the present invention is to provide a method and apparatus which utilizes synchronous luminescence to render medical diagnoses.

Another object of the present invention is to provide a method and apparatus capable of making chemical identifications and/or medical diagnoses with relative speed, improved accuracy and efficiency, thereby leading to significant advances in the understanding of cancer therapy in general and the effective detection of tumors, for example.

These and other objects of the invention are met by providing a method of testing a tissue sample which includes the steps of exposing the tissue sample to an excitation radiation and thereby generating an emission radiation, synchronously scanning the wavelength of the excitation radiation and the wavelength of the emission radiation to produce a spectrum, and correlating the spectrum to a condition of the tissue sample.

Other objects, advantages and salient features of the invention will become apparent from the following detailed description, which, taken in conjunction with the annexed drawings, discloses preferred embodiments of the invention.

DETAILED DESCRIPTION OF THE PREFERRED EMBODIMENT

The present invention combines the high intensity of a laser at the excitation source with the improved selectivity of the synchronous luminescence (SL) technique to perform chemical and biomedical diagnostics. The general theory of the SL method has been described previously in "Synchronous Excitation Spectroscopy," by T. Vo-Dinh, *Modern Fluorescence Spectroscopy*, Chapter 5, Ed. by E. L. Wehry (Plenum Publ. Corp. 1981), which is incorporated herein by reference.

Figure 1:
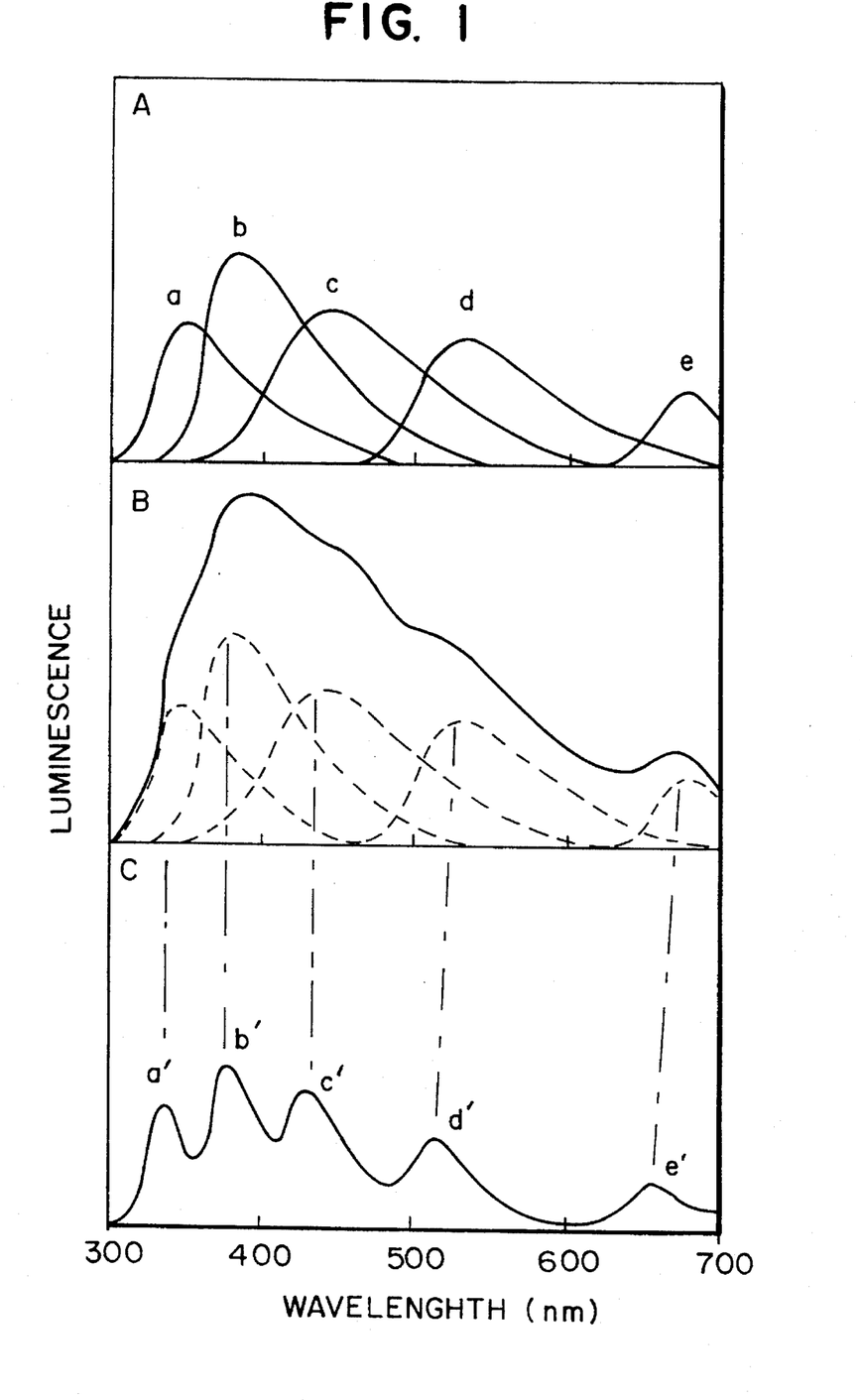
FIGS. 1A–1C is a composite graph showing fluorescence spectra of individual components of tissue, using conventional (i.e., fixed excitation) laser-induced fluorescence and using laser-induced synchronous luminescence of the present invention.

The principal of the synchronous luminescence approach for diagnostics of normal and cancer tissues is illustrated in FIG. 1. One of the problems of fluorescence technique as it is used currently is the fixed wavelength excitation source (e.g., a laser).

Fluorescence from tissues originate from many biological components (e.g., NADH, prophyrins, etc.). Each component has specific absorption and emission spectra occurring at determined spectral ranges, as seen in section "A" of FIG. 1. The spectra illustrated in A are as follows:

a=tryptophan
b=collagen
c=NADH
d=FAD
e=porphyrin

Thus, each curve of A represents the fluorescence of individual components in tissues which might be sampled for the presence of an abnormality, such as a malignancy. ("NADH" stands for nicotiamide ademine dinucleotide, and "FAD" stands for Flavin adenine dinucleotide)

In conventional laser-induced fluorescence (LIF), the laser excitation emission line is fixed (e.g., 337 nm for the nitrogen laser; 325 nm for the helium-cadmium laser). When a fixed laser line is used it is difficult, if not impossible, to excite all the biological components under optimal conditions. Another important limitation of conventional LIF is due to the fact that the fluorescence from tissues arises from the emission of different species, resulting in spectra that are poorly resolved and featureless because of spectral overlap between the emissions from individual components, as seen in the "B" section of FIG. 1. The laser used in LIF can only improve the sensitivity but does not enhance the selectivity.

With the present synchronous luminescence technique, both $\lambda_{em}$ and $\lambda_{ex}$ are scanned synchronously with a constant interval between the two wavelengths ($\Delta\lambda=\lambda_{em}-\lambda_{ex}$). Since the synchronous luminescence spectrum of each component becomes sharper due to the band-narrowing effect of the synchronous luminescence technique, the resulting fluorescence spectrum of the tissues sampled becomes more resolved with sharp peaks that are readily identified. These can be seen in section "C" of FIG. 1 as peaks a', b', c', d', and e'.

The present use of laser-induced synchronous luminescence (LISL) can provide a better spectral signature of tumors and normal tissues. Many subtle spectral features that are indiscernible in conventional LIF spectra can be revealed in the present LISL technique.

Figure 2:
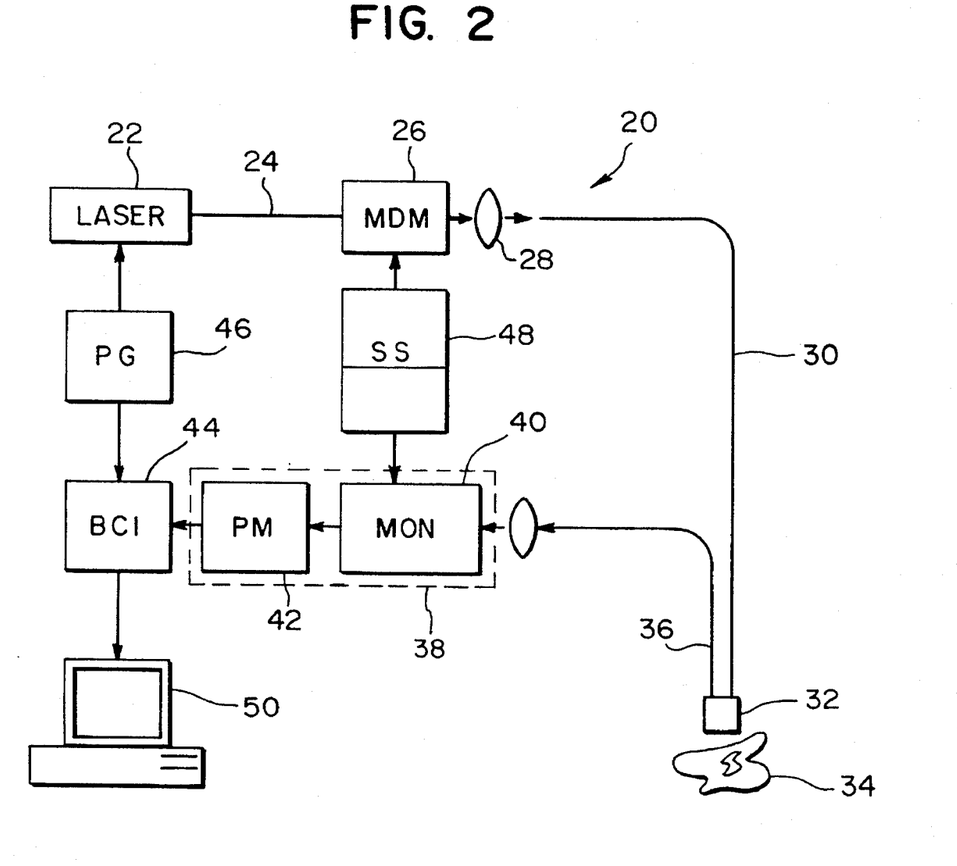
FIG. 2 is a schematic view of a first preferred embodiment of an instrument capable of making chemical and biomedical identifications according to the present invention.

An instrument 20 capable of effecting LISL technique is shown schematically in FIG. 2. The instrument includes a laser 22 outputting a beam 24 having a given wavelength. The laser 20 could be a portable pulsed nitrogen laser, for example.

The output beam 24 is coupled to means 26 for changing the wavelength of the output beam 24. In the illustrated embodiment of FIG. 2, the means is a multi-dye module (MDM) 26. The output of the MDM 26 is delivered, through a focusing lens 28, to an optical fiber (or fibers) 30. The optical fiber 30 can be a single fiber of, for example, 600–µm diameter quartz optical fiber, or multi-fiber bundle could be employed. This fiber or fibers transmits the excitation radiation to the sample being investigated.

The optical fiber 30 transmits the output beam to a probe 32 juxtaposed a sample 34. The probe 32 can be inserted into the working channels of an endoscope for in vivo measurements.

An optical fiber (or fibers) 36 transmits the fluorescence of the sample 34 to detector means 38. The detector means 38 includes a monochromator (MON) 40 and a photomultiplier (PM) 42. A boxcar integrator (BCI) 44, synchronized with the laser pulse via a pulse generator (PG) 46 acting as a trigger is used to record and process the fluorescence signal. A synchronous scanning device (SC) 48 ensures that the excitation radiation ($\lambda_{ex}$) and the emission radiation ($\Delta_{em}$) are maintained at a constant interval ($\Delta\lambda$). A portable computer 50, or other suitable data collection, analysis and/or display devices, can be used to generate the synchronous luminescence spectra such as that which is illustrated in the C section of FIG. 1.

Testing can also be performed to confirm the presence of certain chemicals in the sample 34. In one experiment, a prototype of the instrument 20 was able to detect 680 zeptomoles ($10^{-21}$ moles) of tetracene.

A diagnosis of the sample 34 can be made by comparing the spectra of the sample to spectra for healthy tissue samples, for example. Further programming of the computer 50 could render comparison and diagnoses automatic by computer-assisted comparison of test spectra to pre-recorded or baseline spectra.

Figure 3:
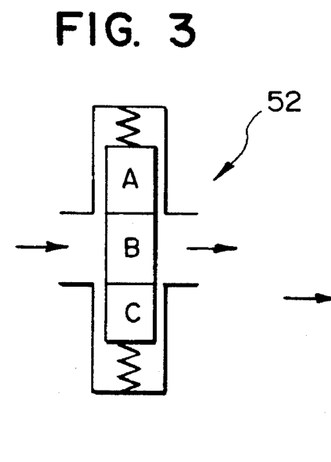
FIG. 3 is a schematic view of a laser dye unit capable of use in the instrument of FIG. 2.

The MDM 26 can be any device capable of producing a suitable range of wavelengths for the scanning of $\lambda_{ex}$. One example is shown in FIG. 3, wherein a laser dye unit 52 includes three dye cells A, B and C, each containing a dye capable of producing a range of excitation wavelengths. For example, if the laser source is a nitrogen pump laser of 337 nm, the dye in cell A could be chosen to produce a range of wavelengths from 350–390 nm. The dye in cell B could be chosen to produce a 390–420 nm range, and the dye in cell C could be chosen to produce a 420–450 nm range. The dye cells are mounted in a quartz cuvette, through which pump laser output passes. Springs on opposite sides of the dye cells help position the cells in the optical path of the pump laser. A motor of the synchronous scanning system 48 changes the dye cells and adjusts the grating of the dye system according to the desired scanning program.

Figure 4:
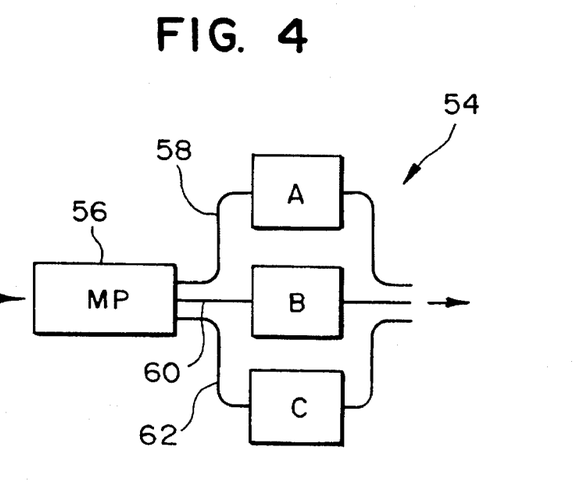
FIG. 4 is a schematic view of an alternative laser dye unit.

An alternative embodiment of a laser dye unit 54 is shown in FIG. 4. The unit 54 includes a fiber optic multiplexer (MP) 56 which delivers the pump laser output to one of the three dye cells A, B, and C through respective optical fibers 58, 60 and 62.

Figure 5:
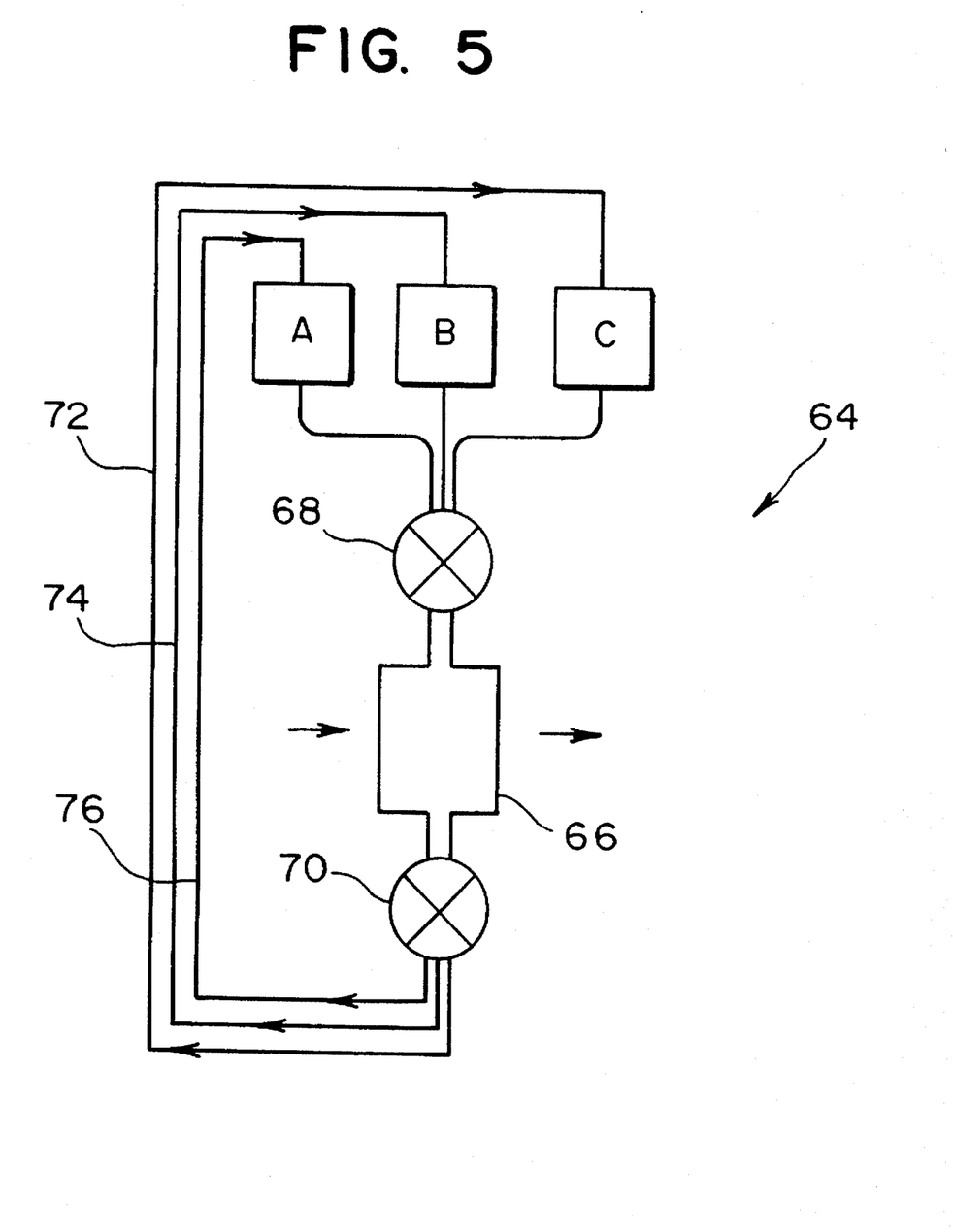
FIG. 5 is a schematic view of another alternative laser dye unit.

A further alternative embodiment of a laser dye unit 64 is shown in FIG. 5. Dye from one of the three dye cells A, B, and C is selectively delivered to a flow cell 66. Flow control valves 68 and 70 are selectively actuated to deliver dye from either of the cells A, B, and C. After use, the dye is returned to the cells through appropriate conduits 72, 74 and 76. Control of the valves, and circulating pumps (not shown) can be through the computer 50 of FIG. 2.

Figure 6:
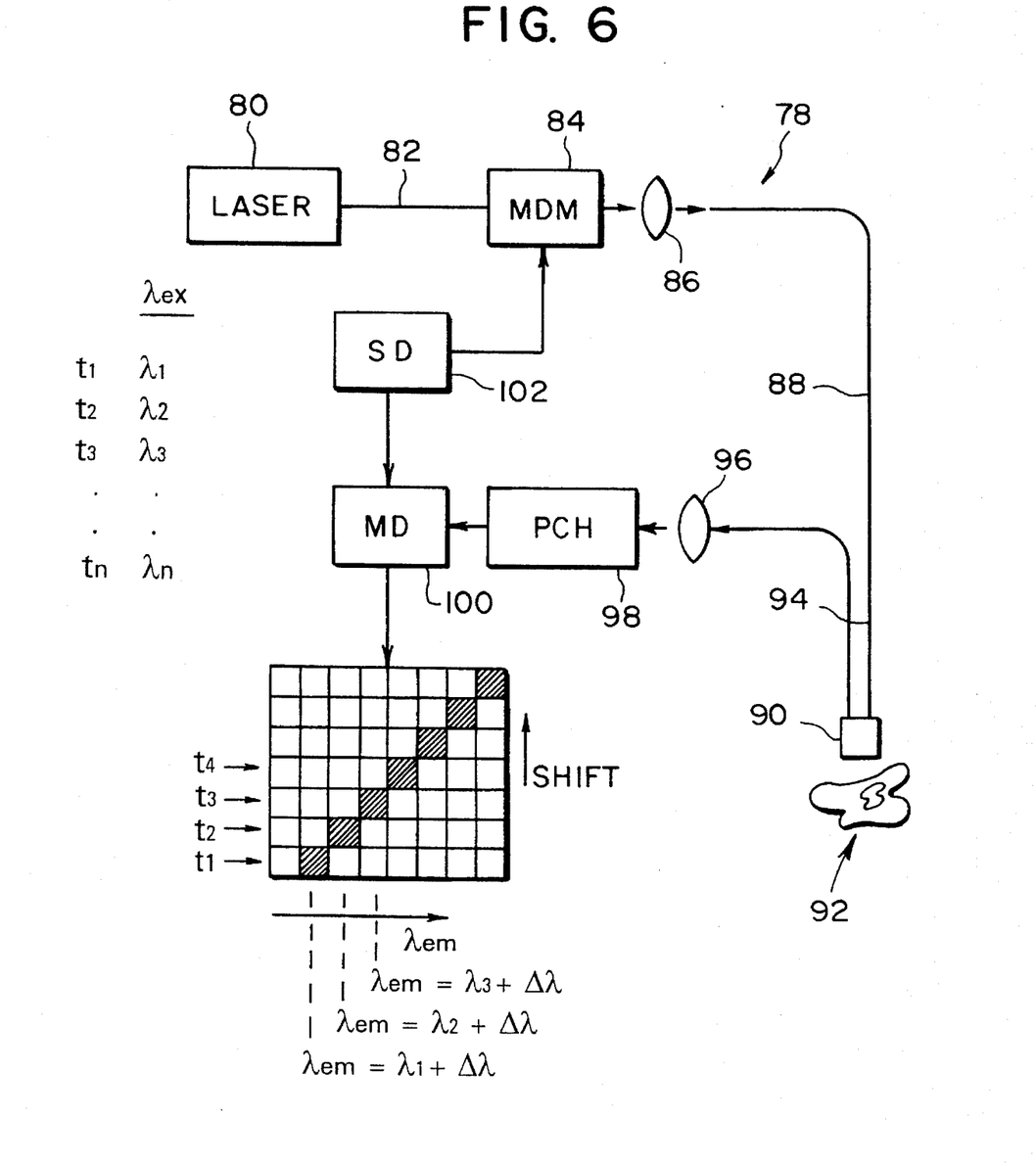
FIG. 6 is a schematic view of another preferred embodiment of an instrument for making chemical and biomedical identifications according to the present invention.

Another embodiment of an instrument 78 is illustrated in FIG. 6. The instrument 78 includes a laser source 80 which produces a pulsed beam 82. The beam 82 passes through a multiple dye module (MDM) 84. The scanning laser excitation radiation is delivered through focusing optics 86 and an optical fiber 88 to a probe 90 juxtaposed a sample 92.

Emission radiation is picked up by optical fiber 94 and delivered through focusing optics 96 to a polychromator (PCH) 98 and multichannel detector (MD) 100. The multichannel detector 100 can be a photodiode array, charge coupled device (CCD), or other similar devices.

A synchronizing device (SD) 102 synchronizes the scanning of $\lambda_{ex}$ with data acquisition of the multichannel detector. In this embodiment, the multichannel detector 100 produces a synchronous luminescence signal based on the black boxes shown in FIG. 6. This data can be collected by a personal computer which controls the synchronizing device 102 and displays and/or stores the synchronous luminescence signal. At each time, $t_n$, the excitation wavelength, $\lambda_n$ changes in a gradual progression. The synchronizing device 102 maintains a constant interval, $\Delta\lambda$, between the emission radiation and the excitation radiation. Note that the laser 22 and the MDM 26 of FIG. 2, or the laser 80 and the MDM 84 of FIG. 6 can be replaced by solid state scanning laser (e.g., titanium saphire laser).

Figure 7:
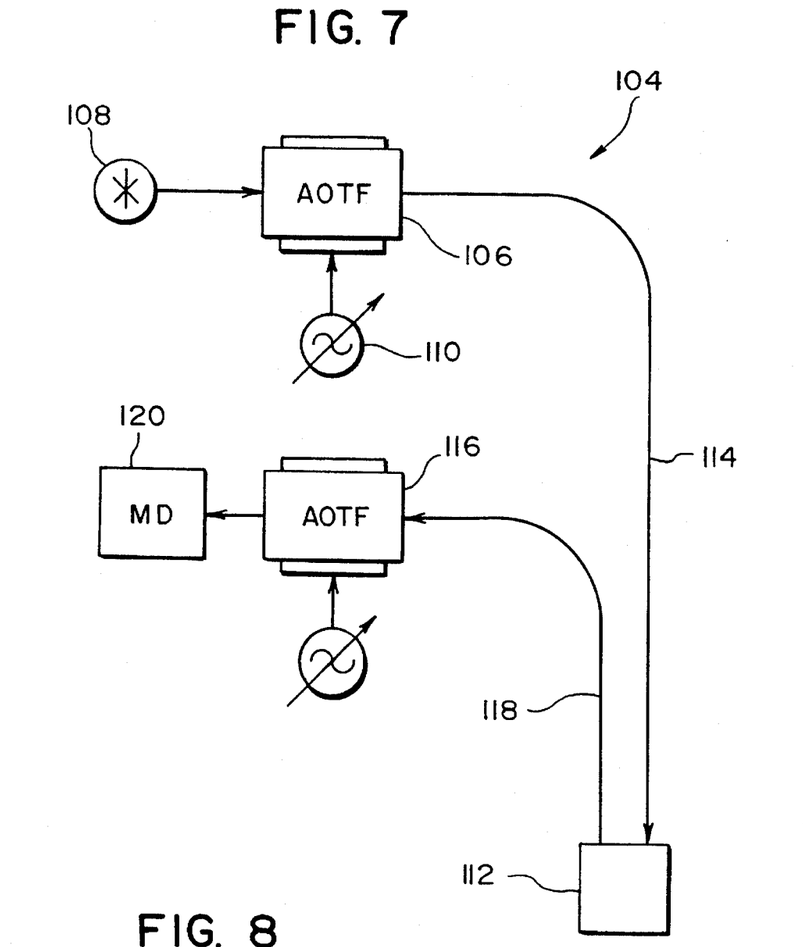
FIG. 7 is a schematic view of another preferred embodiment of an instrument for making chemical and biomedical identifications according to the present invention.

The instrument 104 shown in FIG. 7 uses an acousto-optic tunable filter 106 to scan the frequency of a light source 108. The light source 108 can be either a broad-band conventional light (e.g., xenon lamp) or a laser equipped with a dye module having a broad-band output (i.e., non scanning). The ATOF 106 is an electronically tunable spectral bandpass filter which can operate from the UV to the infrared regions of the optical spectrum. It operates via the interaction of light with a traveling acoustic wave through an anisotropic medium. An acoustic transducer is mounted on one end of a crystal, while an acoustic absorber is mounted on the other end. The transducer converts a high-frequency rf signal, from rf source 110, of a given frequency into a pressure wave which propagates laterally through the crystal at a given velocity $v_a$.

The acoustic absorber at the opposite end of the crystal serves to eliminate acoustic reflections which corrupt the primary acoustic waveform. The diffracted wavelengths are self-selected within the crystal to satisfy the momentum conservation between the incident $k_i$ and the diffracted $k_d$ photon wave vectors and the acoustic wave vector $k_a$ as follows:

$$k_d = k_i \pm k_a$$

One can achieve optical tuning by changing the rf frequency $f_a$ which is related to $\lambda$ as follows:

$$\lambda = v_a(n_o - n_o)a/f_a$$

where $n_o$ and $n_o$ are the refractive indices of the extraordinary and ordinary wave, respectively, and a is a parameter depending upon the design of the AOTF.

The acoustic wave may be considered as the means for generating a transmission grating within the optical crystal. Instead of varying the angle of the incident beam, as would be the case for a normal diffraction grating in order to achieve wavelength selectivity, one varies the frequency of the electrical drive signal, allowing light of different wavelengths to be diffracted at the same angle. Hence with a fixed orientation of the crystal and the use of an rf generator, a tunable optical source is readily created from a broad-band source 108.

As seen in FIG. 7, the output of the ATOF 106 is the excitation radiation ($\lambda_{ex}$) which is delivered to a probe 112 through an optical fiber 114. Emission radiation ($\lambda_{em}$) is delivered to a second ATOF 116 through optical fiber 118. Two rf signals are generated for excitation ($\lambda_{ex}$) and emission ($\lambda_{em} = \lambda_{ex} + \Delta\lambda$) scanning. The output of the emission ATOF is delivered to a photodetector or a Suitable multichannel detector (MD) 120, such as a CCD or PDA for spectral imaging.

Figure 8:
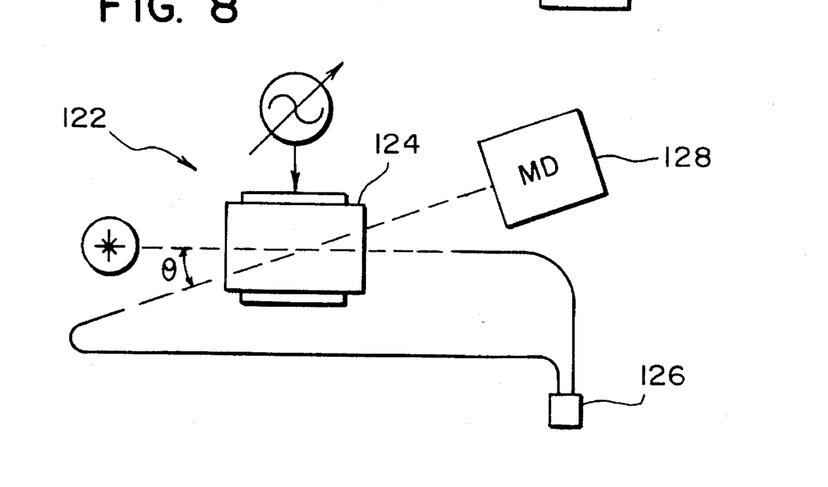
FIG. 8 is a schematic view of another preferred embodiment of an instrument for making chemical and biomedical identifications according to the present invention.

A variation of the FIG. 7 embodiment can be seen in FIG. 8, wherein an instrument 122 includes a single ATOF 124 provides means for scanning the frequency of the excitation radiation ($\lambda_{ex}$) delivered to a probe 126. Emission radiation ($\lambda_{em}$) is fed back through the ATOF 124 at an appropriate angle $\theta$ relative to the excitation path passing through the crystal of the ATOF 124. The crystal in the ATOF is made of $TeO_2$, or other material of suitable properties. The angle $\theta$ is chosen so that $\lambda_{em} = \lambda_{ex} + \Delta\lambda$. Thus, in the embodiment of FIG. 8, the ATOF 124 is used both for excitation and emission. By selecting different angles of diffraction for emission and excitation, one can select $\lambda_1$ for excitation (related to $rf_1$) and $\lambda_1 + \Delta\lambda$ for emission using a different diffraction angle for emission. As in the FIG. 7 embodiment, a single-channel detector or a multichannel detector (MD) 128 is used to receive the emission signal.

Figure 9:
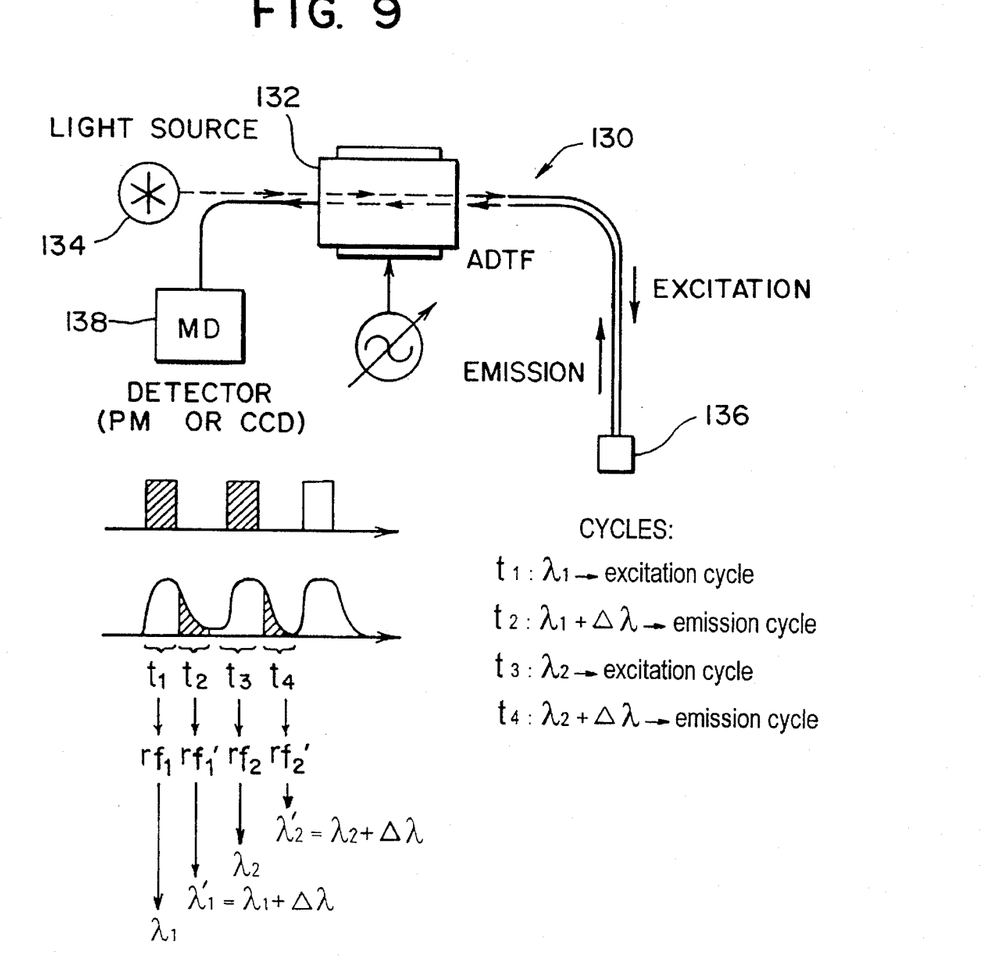
FIG. 9 is a schematic view of another preferred embodiment of an instrument for making chemical and biomedical identifications according to the present invention.

In the embodiment of FIG. 9, the instrument 130 also uses a single ATOF 132 which scans the wavelength of the light source 134. The rf source sends two rf signals alternately into the ATOF 132. By chopping and gated detection, the ATOF 132 can transmit excitation and emission radiation alternatively. As in the previous embodiments, a probe 136 can be juxtaposed any test sample of interest, and the emission radiation is detected with a multichannel detector 138, such as a CCD.

Figure 10:
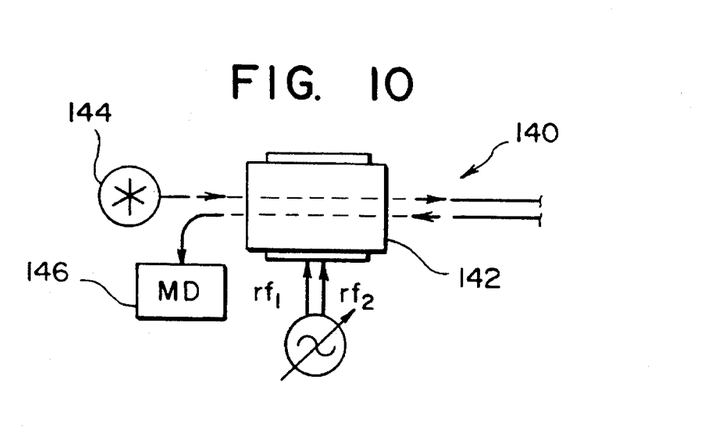
FIG. 10 is a schematic view of another preferred embodiment Of an instrument for making chemical and biomedical identifications according to the present invention.

In the embodiment of FIG. 10, the instrument 140 uses a single ATOF 142 having a rf source which provides two simultaneous outputs $rf_1$ and $rf_2$. The $rf_1$ signal produces an excitation radiation ($\lambda_1$), and $rf_2$ produces the emission radiation ($\lambda_2 = \lambda_1 + \Delta\lambda$). A light source 144 and MD 146 are provided as in the previous embodiments. The intensity of the diffracted beam is controlled by varying the amplitude or the amount of rf power applied to the crystal of the ATOF 142. This approach can also be used to rapidly modulate, or chop the filtered source for lock-in detection schemes.

Further variations of the ATOF embodiments include integration of the ATOF with a laser dye device, instead of gratings, for optical tuning. Also, ATOF devices can be integrated to multichannel detectors (PDA, CCD) instead of photomultiplexers in order to detect two-dimensional SL imaging spectra, as in the FIG. 6 embodiment.

The present invention is effective in cancer tumor diagnostics. It offers more selectivity as compared with conventional fixed-excitation laser-induced fluorescence techniques. Subtle differences in spectral signatures of normal and cancer tissues can be detected more easily. The present invention combines the improved selectivity of synchronous scanning, the high intensity of laser excitation and the fast scanning of AOTF's.

The various embodiments described herein can be assembled from commercially available components. For example, and referring to FIG. 2, the laser 22 could be a small nitrogen/dye laser system available as models VSL-337 and VSL-DYE from Laser Science of Newton, Mass. (USA). The monochromator 38 used to collect fluorescence radiation can be a 10-cm focal length model H-10 monochromator made by ISA of Edison, N.J. (USA). The detector 42 can be a Hamamatsu Model R760 photomultiplier.

The pulse energy of the tunable laser output used in some experiments was 5–10 µJ/pulse over the range of wavelengths used in the experiments. The stepper motors used to drive both the dye module 26 and the monochromator 38 used digital (TTL) output pulses from an ADC card by MetraByte Corporation of Taunton, Mass. (USA), model DASH-16F. The same card was used for timing and to collect the analog signal. The signal from the photomultiplier 38 is preferably amplified with a fast preamplifier, such as a Stanford Research Systems Model SR445, DC-300 MHz, before being input to the boxcar integrator 44. The boxcar could be a Stanford Model SR250.

Figure 11:
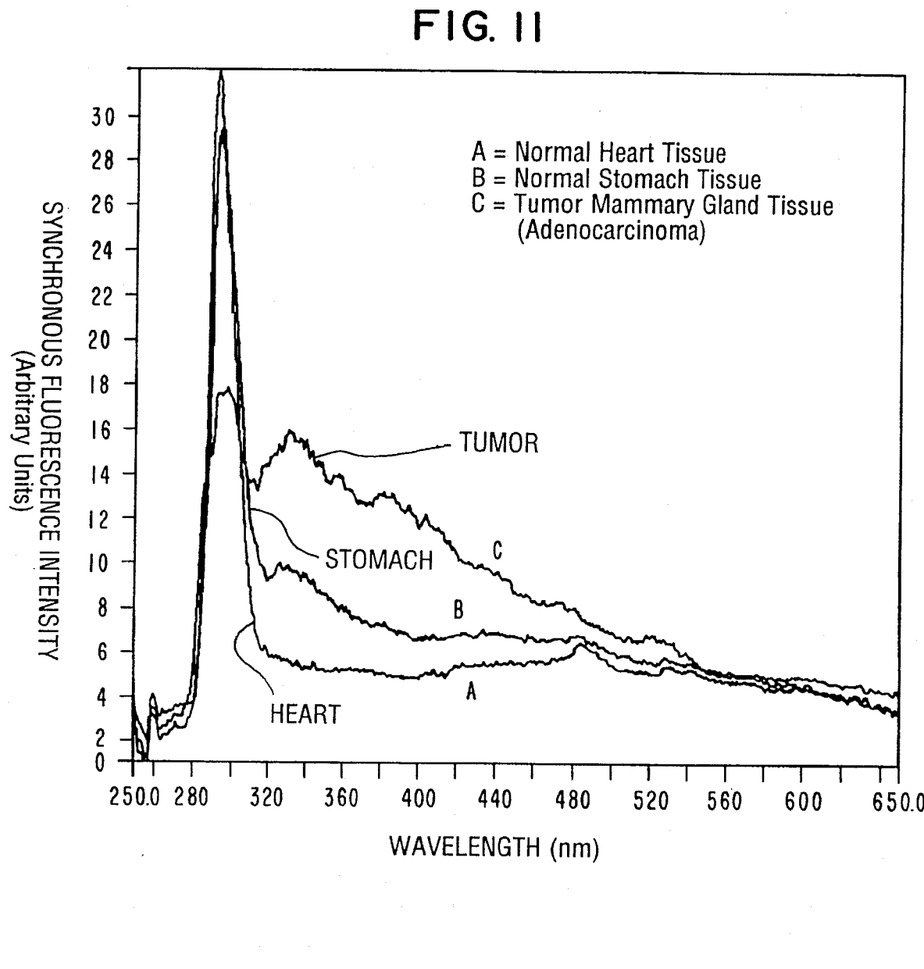
FIG. 11 is a display showing examples of synchronous luminescence of various types of tissues.

In experiments conducted using the FIG. 2 instrument, the scan speed was 10 nm/s. The laser repetition rate was 15 Hz and the time constant at the boxcar was 0.2 s (3 pulse average). After scans, all spectra were smoothed using a second-order Savitzky-Golay 37 point-smoothing algorithm. FIG. 11 is a display, as would be generated by a computer coupled to the instrument of the present invention, showing examples of synchronous luminescence spectra of various types of tissues. For the display of FIG. 11, a wavelength difference between excitation and emission of 10 nm was used.

The results displayed in FIG. 11 indicate that it is possible to use the different spectral profiles of the synchronous luminescence (SL) signal to characterize the tissues. Although the examples show results with tissue samples homogenized in solution, a similar measurement approach can also be used directly on tissue samples in vivo.

Normal and cancerous tissues can be better differentiated by the SL signals. It is expected that the techniques and instruments described herein can be applied to a wide variety of applications including, for example, diagnosis of skin, colon, stomach, cervical cancers, etc.

Figure 12:
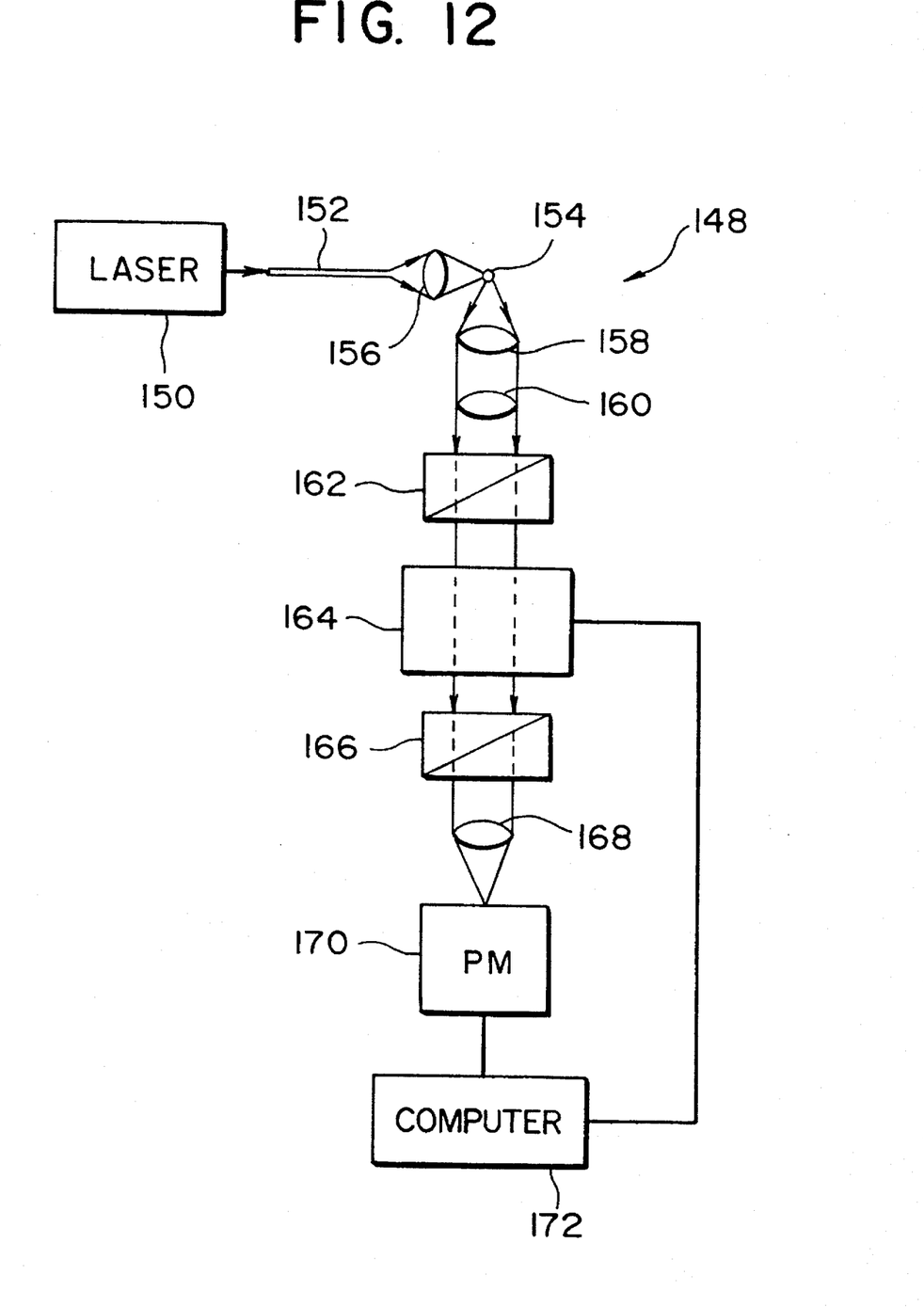
FIG. 12 is a schematic view of another preferred embodiment of an instrument for making chemical and biomedical identifications according to the present invention.

The ATOF embodiments described herein also can be assembled from commercially available components. In the embodiment of FIG. 12, the instrument 148 includes a helium-cadmium laser 150 (Omnichrome model 3074-6) whose output is directed to a silica clad-silica core optical fiber 152. The laser radiation emitted from the distal end of the optical fiber 152 is focused onto a sample 154, such as a quartz cuvette containing a sample solution, or a sample tissue) by a quartz lens 156.

The luminescence signal from the sample is collected at a right angle to the excitation beam. A pair of quartz lens 158 and 160 (f/4) are used to form a roughly collimated beam. A Glen-Taylor (polarizing) prism 162 allows only linearly polarized light into an AOTF 164 (Brimrose model QZAF-0.25-0.65). The polarization angle of the prism 162 is aligned with the polarization axis of the AOTF 164.

A second Glen-Taylor prism 166 is oriented orthogonally to the first prism 162, blocking the non-diffracted light.. A quartz lens 168 focuses the filtered light onto a photomultiplier (PM) tube 170 (Hamamatsu model R928).

The AOTF 166 can have an operating spectral range of 250–650 nm. The spectral resolution is 0.9 nm and the diffraction efficiency is 25% at 400 nm. The radio frequency control signal applied to the AOTF is controlled by a DOS-based computer 172 using a 16-bit computer controller board.

The Signal from the PM tube 170 is converted from analog to digital and then processed by the computer 172 which is programmed to control the AOTF for various scan modes. A real time data display mode can also be incorporated into the program.

Figure 13:
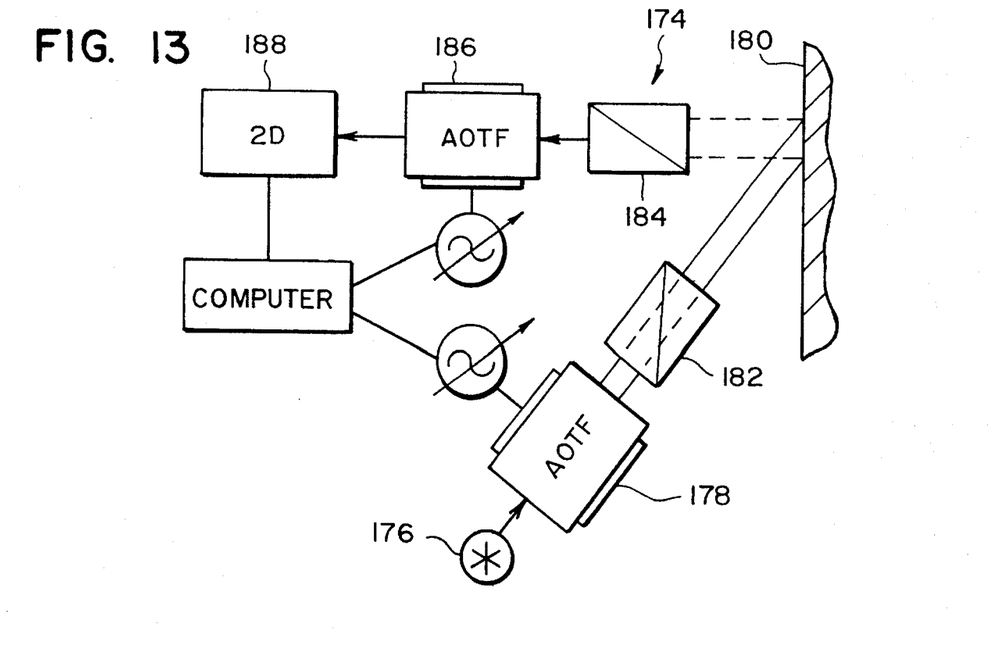
FIG. 13 is a schematic view of another preferred embodiment of an instrument for making chemical and biomedical identifications according to the present invention.

In FIG. 13 the laser is replaced by a broad-band light source equipped with a second AOTF. Both emission and excitation AOTFs can be scanned synchronously.

The use of an optical fiber in the embodiments using one or more AOTF's can be avoided. As shown in the embodiment of FIG. 13, the instrument 174 includes a light source 176 and excitation radiation AOTF 178. A surface 180 to be analyzed receives the scanning excitation radiation after passing through collimating optic 182. Emission radiation passes through collimating optic 184 and then to emission AOTF 186, and then to a two-dimensional detector (2D) 188. These signals are then converted into spectra by a computer 190, which also controls the scanning of the two AOTFs 178 and 186. Each point of the surface has a synchronous luminescence spectrum. In this embodiment, the light source is made to illuminate the area of interest, rather than a specific point. Thus, this type of instrument can be used to diagnose large areas of sample tissues since it allows the collection of the entire synchronous luminescence spectrum of every point on the area illuminated by the light source and under the field of view of the CCD detection system.

While no fiber optics were used in the FIG. 13 embodiment, a coherent bundle of fibers could be used to transmit individual pixels of images in the detection process.

Figure 14:
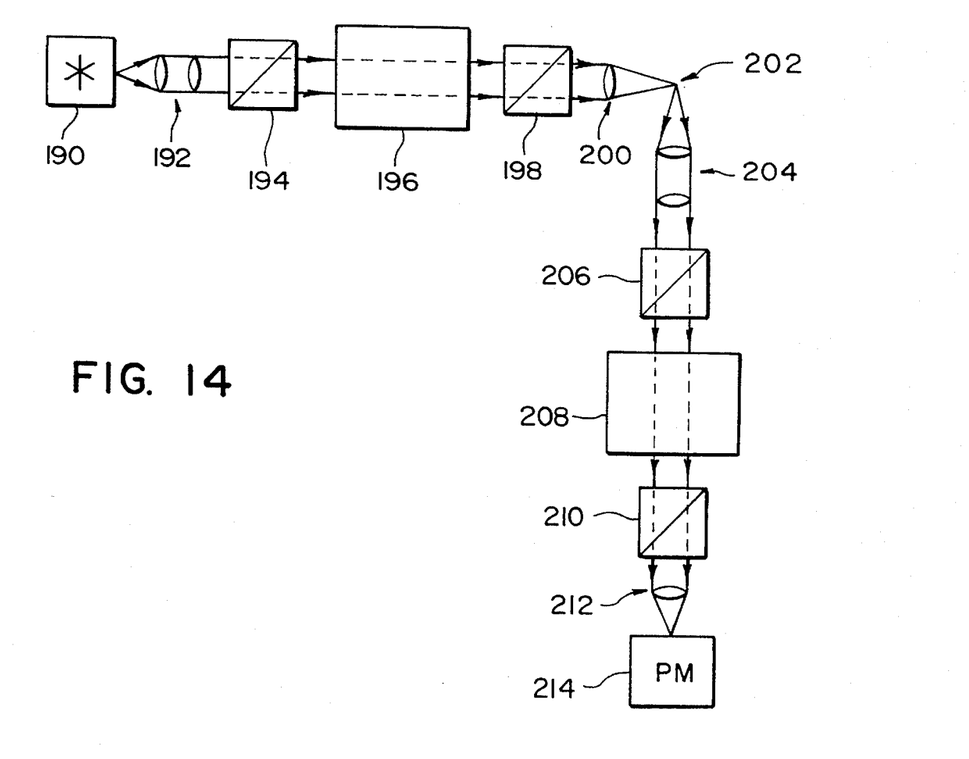
FIG. 14 is a schematic view of another preferred embodiment of an instrument for making chemical and biomedical identifications according to the present invention.

The embodiment of FIG. 14 includes a continuum light source 190, such as a high pressure xenon lamp. The lamp output passes through a pair of quartz lenses 192, which form a roughly collimated beam. A Glen-Taylor (polarizing) prism 194 is used to allow only linearly polarized light into an AOTF 196.

The output of the AOTF 196 passes through a second prism 198 and is focused by a lens 200 to a point 202 on a tissue sample. A second pair of quartz lenses 204 form a roughly collimated beam which passes through another polarizing prism 206. Emission radiation from the sample at point 202 is thus scanned by a second AOTF 208.

Prism 210 is oriented orthogonally relative to the prism 206 to block the non-diffracted light. A lens 212 is positioned to focus the filtered light onto a photomultiplier tube (PM) 214. Synchronous luminescence spectra can be produced and analyzed by coupling the output of the photomultiplier to a suitable analyzer, such as a personal computer with data acquisition capabilities.

While advantageous embodiments have been chosen to illustrate the invention, it will be understood by those skilled in the art that various changes and modifications can be made therein without departing from the scope of the invention as defined in the appended claims.

What is claimed is:

1. A method of testing a tissue sample to determine malignant or pre-malignant abnormality, comprising the steps of:

exposing the tissue sample to an excitation radiation and thereby generating an emission radiation;

synchronously scanning the wavelength of the excitation radiation and the wavelength of the emission radiation to produce a spectrum; and correlating the spectrum to a malignancy condition of the tissue sample.

2. The method according to claim 1, wherein the synchronously scanning step comprises maintaining a constant interval between the wavelength of the excitation radiation and the emission radiation during synchronous scanning.

3. The method according to claim 1, wherein the exposing step comprises directing an output beam from a laser light source to the tissue sample through at least one optical fiber.

4. The method according to claim 3, further comprising directing the output of the laser light source into a probe disposed in vivo next to the tissue sample.

5. The method according to claim 3, wherein the scanning step further comprises directing the output beam of the laser source through a dye module having a plurality of dyes, and changing the dyes to achieve a range of excitation wavelengths.

6. The method according to claim 3, wherein the scanning step further comprises directing the output beam of the laser source through a dye container, and selectively moving a plurality of dyes into the dye container to achieve a range of excitation wavelengths.

7. The method according to claim 1, wherein the synchronous scanning step comprises directing the excitation radiation into a first acousto-optic tunable filter, and changing an input radio frequency of the first filter to achieve a range of excitation wavelengths.

8. The method according to claim 7, wherein the synchronous scanning step further comprises directing the emission radiation into a second acousto-optic tunable filter, and changing an input radio frequency of the second filter to achieve a range of emission wavelengths.

9. The method according to claim 7, wherein the synchronous scanning step further comprises directing the emission radiation into the first filter at an angle relative to the excitation radiation.

10. The method according to claim 7, wherein the synchronous scanning step further comprises directing the emission radiation into the first filter, alternately providing two radio frequency signals to the first filter to alternately pass the excitation and emission radiations through the first filter, and alternately detecting the emission radiation when the first filter is not transmitting the excitation radiation.

* * * * *